United States Patent [19]

Case

[11] 4,405,317
[45] Sep. 20, 1983

[54] SYRINGE ASSEMBLY

[75] Inventor: Kirt L. Case, Warsaw, Ind.

[73] Assignee: The West Company, Phoenixville, Pa.

[21] Appl. No.: 306,954

[22] Filed: Sep. 30, 1981

[51] Int. Cl.³ .............................................. A61M 5/00
[52] U.S. Cl. .................................................... 604/90
[58] Field of Search ............ 128/218 R, 218 P, 218 D, 128/218 DA, 218 M, 272.1, 215, 234; 604/90, 91, 92, 89, 82, 48, 56, 416

[56] References Cited

U.S. PATENT DOCUMENTS

| | | | |
|---|---|---|---|
| 3,477,432 | 11/1969 | Shaw | 128/218 M |
| 3,557,787 | 1/1971 | Cohen | 128/218 M X |
| 3,685,514 | 8/1972 | Cheney | 128/218 M |
| 3,718,139 | 2/1973 | Hanford | 128/218 M |
| 4,331,146 | 5/1982 | Brignola | 128/218 DA |

Primary Examiner—John D. Yasko
Attorney, Agent, or Firm—Eugene E. Renz, Jr.

[57] ABSTRACT

In a syringe assembly comprising an outer barrel for a powder medicament, an inner barrel telescopically mounted in the outer barrel for diluent, seal means isolating the powder and diluent compartments comprising a plug member made of a resilient material sealingly engaging in the discharge opening of the inner barrel, plunger means mounted on the discharge end of the inner barrel including a hollow plug chamber closed at one end remote from the discharge end of the inner barrel by a wall having a plurality of discharge openings therein, said plug adapted upon pressure buildup in the inner barrel to be displaced axially outwardly into said plug chamber to permit flow of diluent from the inner barrel to the powder compartment.

6 Claims, 5 Drawing Figures

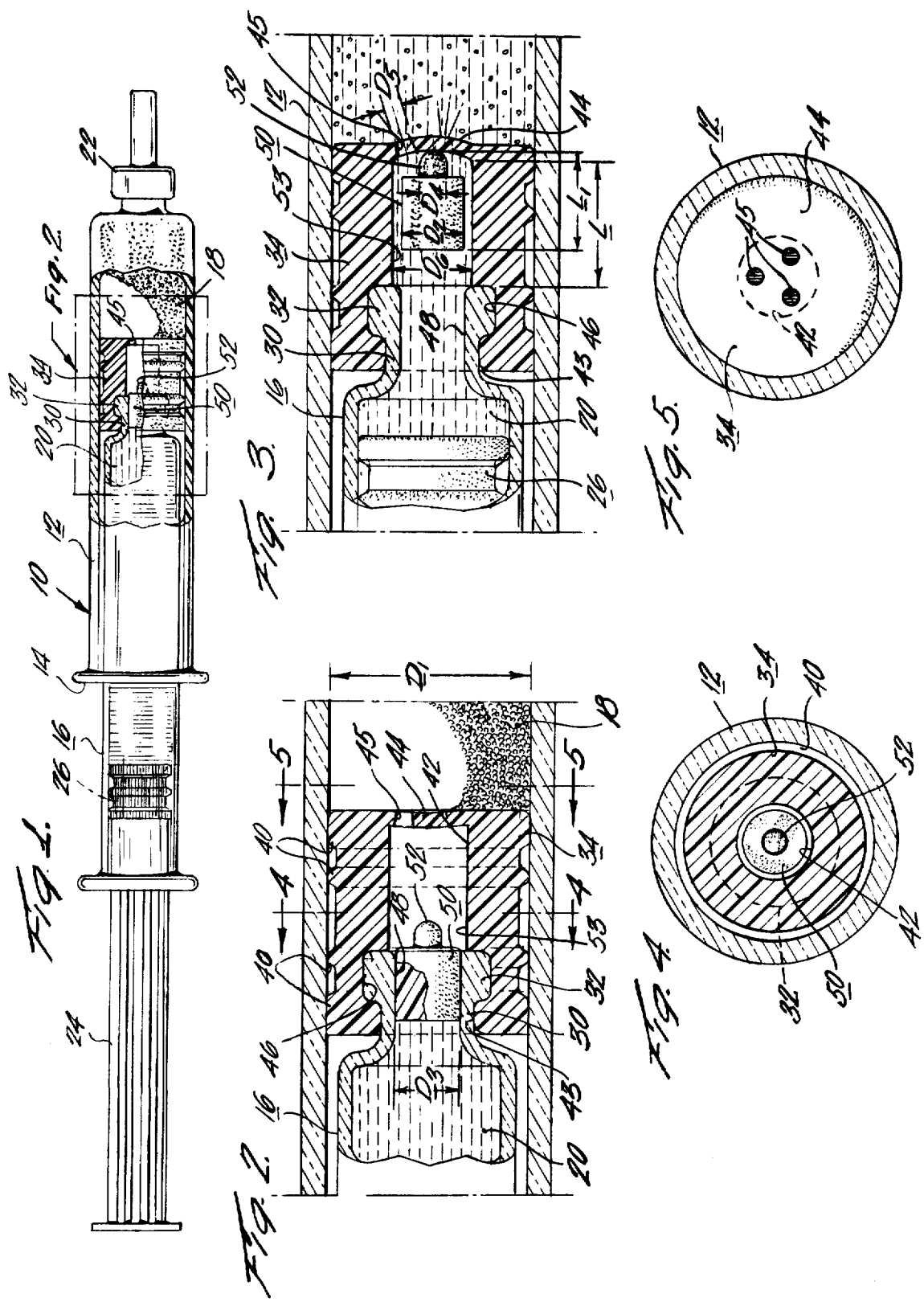

SYRINGE ASSEMBLY

BACKGROUND AND SUMMARY OF THE INVENTION

The present invention relates to syringe assemblies for administering fluid medications to patients and more specifically to syringe assemblies commonly referred to as two compartment syringes wherein the powder medicament and diluent are isolated in separate compartments of the syringe for storage purposes and including means for mixing a powder medicament and diluent just prior to use.

Two compartment syringes are not new per se. These syringe assemblies generally comprise an outer barrel, vial or container for the powder medicament, and inner barrel, vial, or container telescopically mounted in the outer barrel for the diluent and a plunger moveable axially in the inner barrel for mixing and discharging the medicament through a needle mounted at the discharge end of the outer barrel. Generally, these assemblies include some form of sealing means mounted at the discharge end of the inner barrel which normally isolates the diluent and powder medicament until ready for use. In some instances the sealing means is in the form of a diaphragm which is supported over the discharge end of the inner barrel and which upon increase of hydraulic or fluid pressure in the inner barrel caused by actuation of the plunger either releases or is burst to permit flow of diluent to the powder medicament chamber for preparation of the medicament. Even though these assemblies are generally satisfactory, it has been found that they do have certain disadvantages and drawbacks. For example, the bursting diaphragm type presents the problem of particulate matter mixing with the medicament which can cause difficulty in discharging the syringe contents and there is also the danger of injecting particulate matter into the patient.

Additionally, it has been found that in some instances these sealing arrangements do not provide an adequate moisture-vapor barrier and consequently the assemblies do not possess the necessary desired long shelf life. It is noted that migration of vapor to the powder medicament may effect its efficacy.

An example of a two compartment syringe incorporating bursting and so-called slide aside diaphragms is shown and described in the Brignola application, Ser. No. 06/034,461 now U.S. Pat. No. 4,331,146 entitled SYRINGE ASSEMBLY, owned by the assignee of the present application. In the two compartment syringes illustrated, the sealing means is in the form of a thin Teflon diaphragm which is supported over the discharge end of the inner barrel by a rubber plunger which has a through opening. In one form of the diaphragm, the return flange is of uniform configuration so that actuation of the plunger axially in the inner barrel causing increase in fluid or hydraulic pressure bursts the diaphragm and diluent can flow freely to the powder compartment. Bursting, of course, may present the problem and danger of particulate matter and it is therefore somewhat undesirable. In another form, the return flange of the diaphragm is of a predetermined configuration so that the seating force is non-uniform about the periphery and hence when the internal hydraulic pressure increases, the diaphragm does not burst but displaces laterally to permit flow of diluent to the powder compartment. In some instances, the entire diaphragm may be displaced and this presents the problem of clogging or jamming the discharge opening in the outer barrel and prevent easy discharge of the mixed medicament. Further, the barrels are usually made of polymerized glass and consequently the desired inert Teflon diaphragm is difficult to seat accurately over the discharge end of the inner barrel with the inner plunger engaging over it since it tends to slip and not adhere sufficiently to the glass. Thus assembly is tedious and time consuming.

In accordance with another two compartment syringe shown in German Pat. No. 1,491,785 the inner barrel has a pintle which projects through an opening in a diaphragm snugly seated over the discharge end of the inner barrel and the inner barrel is provided with a series of small discharge ports circumferentially spaced outboard of the centrally disposed pintle. Now fluid pressure acting through these small openings displaces the axial end face of the diaphragm outwardly to permit flow to the powder compartment. Even though this arrangement avoids the problem of particulate matter, it is virtually impossible to provide the necessary tight seal to prevent migration of moisture and thus this syringe has a very short unacceptable shelf life.

The two compartment syringe shown in the Cheney Pat. No. 3,685,514 issued Aug. 22, 1972, shows a similar arrangement. However, in this assembly the inner barrel has a small centrally located discharge port and the diaphragm which snugly embraces the outer discharge end of the inner barrel has a series of circumferentially spaced openings normally confronting the axial end face of the inner barrel radially outwardly of the centrally located discharge port. Thus, when the plunger is actuated to increase hydraulic pressure in the inner barrel, the thin face of the diaphragm is deflected outwardly to permit flow from the central discharge port in the inner barrel to the radially outwardly located discharge openings in the front face of the diaphragm. Here again, there is no problem of particulate matter. However, the seal is not sufficient to ensure a good long shelf life. Furthermore, in both assemblies inadvertent pressure on the actuating plunger during shipment or even while in storage, can result in small quantities of diluent entering the powder chamber and destroying the efficacy of the product. Furthermore, this inadvertent actuation would not be readily ascertainable by the user.

Cohen, U.S. Pat. No. 3,838,689 issued Oct. 1, 1974 for DISPOSABLE SYRINGE WITH SLIT VALVE shows an arrangement wherein the valve or diaphragm separating the two compartments has a slit which normally seals the two compartments and which opens on increase in hydraulic pressure to permit flow of diluent for mixing purposes. Here again, migration of vapor to the powder compartment over a period of time is inevitable and consequently, these syringes have a relatively short, unacceptable shelf life. The slit is usually formed in the plunger-type diaphragm when the elastic material, usually rubber, is in a generally relaxed state and it has been found that the slit tends to reknit or bond itself shut when the plunger is placed under compression in the syringe and consequently the rather thick wall of the plunger is extremely difficult or impossible to burst when it is desired to actuate the syringe. This is particularly true with syringes that have been stored for normal relatively long periods prior to use.

Shaw, U.S. Pat. No. 3,477,432 issued Sept. 21, 1964, shows several embodiments of two compartment syringes. In accordance with one embodiment, the diaphragm at the discharge end of the inner barrel has a hinged plug which frictionally seats in the discharge end to normally seal the two compartments. This is good from the standpoint of eliminating particulate matter but has the shortcoming described above, an inadequate seal.

Ratcliff, et al U.S. Pat. No. 2,869,534 issued Aug. 23, 1957, for INJECTOR shows an arrangement wherein the inner barrel terminates in a nozzle and a cap fits over the nozzle to normally seal the chamber. The cap is discharged completely from the nozzle of the inner barrel upon increased hydraulic pressure in the inner barrel when arming or preparing the syringe for mixing the diluent and powder. The cap floating in the outer chamber may jam the discharge opening and hinder easy discharge of the medicament.

With the above in mind, it is an object of the present invention to provide a new and improved syringe assembly which is characterized by novel features of construction and arrangement providing an effective moisture-vapor barrier between the diluent and powder compartments thereby ensuring a long shelf life and which may be actuated to mix the components without creation of any material particulate matter thereby ensuring the integrity and safety of the product dispensed. To this end, the assembly includes a plug made of a resilient material, such as rubber, which normally seats in the discharge end of the inner barrel having a pintle or teat-like projection on its outer axial end face and a plunger assembly mounted on the discharge end of the inner barrel which snugly engages in the outer barrel and has a chamber formed therein of an axial length greater than the axial length of the plug and of a diameter slightly greater than the diameter of the plug and formed with a series of openings in the front face of the chamber. By this arrangement, when the inner barrel actuating plunger is moved forwardly, the plug is displaced into the plunger chamber and is confined therein in a position to permit flow of the diluent from the inner barrel around the plug to the outer barrel. The teat-like projection engages generally centrally relative to the openings in the front face of the plunger to ensure good flow of diluent around the plug during the mixing cycle. It has been found that this arrangement provides an effective seal and eliminates the problem of particulate matter. Furthermore, the parts of the assembly are relatively easy and economical to make and can be assembled quickly and easily to provide a well-sealed arrangement ensuring long shelf life and also one that eliminates the problems of particulate matter or difficulty in preparing for mixing characteristic of some of the prior syringes discussed above.

DESCRIPTION OF THE DRAWINGS

These and other features of the present invention and various details of the construction and operation thereof are hereinafter more fully set forth with reference to the accompanying drawing, wherein;

FIG. 1 is a side elevational view partly in section of a two compartment syringe in accordance with the present invention;

FIG. 2 is an enlarged fragmentary sectional view of the portion of the assembly shown in broken lines in FIG. 1 with the plug in a seated or sealed position;

FIG. 3 is a view similar to FIG. 2 showing the plug displaced and the actuating plunger fully extended at the termination of the mixing cycle; and FIGS. 4 and 5 are sectional views taken on lines 4—4 and 5—5 respectively of FIG. 2.

DESCRIPTION OF THE PREFERRED EMBODIMENT

Referring now to the drawing and particularly to FIG. 1 thereof, there is shown a syringe assembly in accordance with the present invention generally designated by the numeral 10. The invention has particular application and is shown and described in connection with a two compartment syringe. However, it is to be understood that the invention has also useful application in single compartment syringes. The two compartment syringe includes an outer barrel or container 12 which is open at its inner end as at 14 to telescopically receive an inner barrel or container 16. The two compartment syringe is especially adapted for use with medicament solutions which are not storage stable in the form in which they are to be injected. In the two compartment syringe of the present invention, the stable components of such a medicament solution can be stored separately and can be mixed just prior to use, thereby providing an extended shelf life assembly. In the present instance the outer barrel 12 defines a compartment for housing a granular or liquid substance 18 and the inner barrel 16 defines a compartment containing the liquid diluent 20. The inner and outer barrels are preferably made of glass but may also be constructed of a suitable transparent plastic material. The outer barrel or container is of conventional construction at its discharge end to mount a cap or cover 22 which normally provides a sealed closure for the discharge end of the outer barrel but which is capable of being readily removed to permit the hub of a needle to be mounted on the extension when the syringe assembly is readied for use. The syringe assembly further includes a plunger rod 24 which mounts at its forward end a standard or conventional plunger 26 and which is axially actuatable in the inner barrel to activate the syringe in the manner described in more detail below. The inner barrel has a reduced neck portion 30 at its discharge end and a radially outwardly directed bead or finish 32.

In accordance with the present invention, a plug and plunger assembly is mounted in the discharge end inner barrel which normally isolates the diluent and powder compartments for extended shelf life. In the present instance the plunger 34 which may be made of a resilient material such as rubber is an elongated generally tubular member having a series of axially spaced ribs 40 on its outer periphery which are of an outer diameter D slightly greater than the inner diameter $D_1$ of the outer barrel to provide a tight seal therebetween and has a generally cylindrical axial bore 42 open at its inner end 43 and closed at its outer end by wall 44 which has a series, in the present instance, three circumferentially spaced ports or openings 45 offset radially from the axial center or axis of the plunger as shown in FIG. 5. An enlarged groove 46 is formed in the bore 42 spaced inwardly from the inner end 43 defining a pocket or seat 46 within which the finish or rib of the inner barrel engages or seats. A generally cylindrical elongated plug 50 is mounted in the discharge opening 48 of the inner barrel and is of a diameter $D_2$ slightly greater than the diameter $D_3$ of the discharge opening 48 in the inner barrel to provide a tight seal. The plug 50 is made of a resilient material such as rubber and has a teat-like projection or pintle 52 in its forward face. When the plunger is seated on the end of the inner barrel, the bore 42 and wall 44 form a confined chamber 53 for the plug 50. The diameter $D_4$ of the pintle 52 is preferably greater than the diameter $D_5$ of the discharge openings 45 in the wall 44 to minimize clogging and maximize flow of diluent through the plunger when the plug is displaced into the plug chamber 53. The pintle 52 which is located on the axis of the plug also spaces the plug body from the plunger discharge openings again to ensure good flow around the plug in the mixing cycle.

The components of the syringe are assembled in the following manner. With the cap 22 in place, the outer barrel 12 is filled with the powder medicament. The plug 50 is then inserted in the discharge end 48 of the inner barrel 16 and fitted over the discharge end. Thereafter the inner barrel 16 is filled with the diluent. The inner barrel, plug and plunger assembly are then positioned or telescoped into the outer barrel 12 a predetermined distance allowing about a twenty percent (20%) head space in front of the powder medicament in the outer barrel as illustrated for example in FIG. 1. The actuating plunger 26 is then fitted into the inner barrel. For shipment and storage, the plunger rod 24 may be shipped or stored separately from the syringe unit and assembled when it is desired to actuate the syringe.

Now when it is desired to mix the diluent and powder medicament, the plunger rod 24 is simply assembled to the actuating plunger 26 and pushed forwardly into the inner barrel. The hydraulic force thus exerted displaces the plug 50 from the discharge end of the inner barrel forwardly into the plunger chamber 53 to the position shown in FIG. 3. Now as the actuating plunger is moved forwardly, the diluent flows around the plug 50 and through the discharge openings 45 in the wall 44 until the diluent barrel has been completely evacuated and as the diluent is expelled it mixes with the powder in the outer barrel. The syringe is now ready for use. Therefore, the cap 22 can be removed and a needle assembled. The empty liquid barrel now becomes the plunger rod and after the needle is assembled to the front end of the outer barrel, the syringe can be evacuated of air and inserted, aspirated and injected in a normal manner. The plug chamber 53 in the plunger as illustrated is an axial length L measured from the front wall 44 to the front edge of the pocket or seat 46 for the inner barrel finish greater than the axial length $L_1$ of the plug 50 measured from the back face to the tip of the teat-like projection 52. The diameter $D_6$ of the plunger chamber 53 is also greater than the plug diameter $D_2$ in its relaxed state to allow flow of diluent around the plug in the manner shown in FIG. 3.

The following is a preferred dimensional relationship of the diameters and axial lengths for a syringe of a given size:

D—Diameter of plunger ribs 40—0.496"
$D_1$—Inner diameter of outer barrel 12—0.476"-0.491"
$D_2$—Diameter of plug body portion 50—0.165"
$D_3$—Diameter of inner barrel discharge-opening 48-0.138"-0.153"
$D_4$—Diameter of plug pintle 52—0.062"
$D_5$—Diameter of plunger dicharge openings 45—0.050"
$D_6$—Diameter of plug chamber 53—0.191"
L—Axial length of plunger plug chamber 53—0.248"
$L_1$—Axial length of plug 5—0.180"

What is claimed is:

1. In a syringe assembly comprising an outer barrel for a powder medicament, an inner barrel telescopically mounted in the outer barrel for diluent, seal means isolating the powder and diluent compartments comprising a plug member made of a resilient material sealingly engaging in the discharge opening of the inner barrel, plunger means mounted on the discharge end of the inner barrel including a hollow plug chamber closed at one end remote from the discharge end of the inner barrel by a wall having a plurality of discharge openings therein, said plug member including a pintle projecting from one axial end face thereof of said plug member of a diameter less than the body portion of said plug member and greater than the discharge openings in said plunger end wall, said plug member adapted upon pressure buildup in the inner barrel to be displaced axially outwardly into said plug chamber to permit flow of diluent from the inner barrel to the powder compartment.

2. In a syringe assembly as claimed in claim 1 wherein said plug includes a pintle projecting from one axial end face thereof of a diameter less than the body portion of said plug member and greater than the discharge openings in said plunger end wall.

3. In a syringe assembly as claimed in claim 1 wherein said discharge openings in the end wall are circumferentially arranged and dispose radially outwardly of the axis of said plug chamber and said pintle is located on the axis of said plug member.

4. In a syringe assembly as claimed in claim 1 wherein the axial length of said plug member is less than the axial length of said plug chamber measured from the discharge end of said inner barrel to the front wall of said plunger.

5. In a syringe assembly as claimed in claim 1 wherein the diameter of said plug chamber is greater than the maximum diameter of said plug body portion in the relaxed state.

6. Displaceable seal means for sealing a discharge end of a barrel for a medicament comprising an elongated generally cylindrical plug member of a predetermined diameter to press fit in the discharge opening of said barrel to provide a seal, a plunger mounted over the discharge end of said barrel having a generally closed plug chamber defined by an axial end wall having a series of discharge openings therein, said plug member including a pintle projecting from one axial end face thereof of said plug member of a diameter less than the body portion of said plug member and greater than the discharge openings in said plunger end wall, said plunger axially displaceable from said discharge opening to engage in said plug chamber upon increase of hydraulic pressure in said barrel to permit flow of product through the discharge end of said barrel.

* * * * *